(12) United States Patent
Cho et al.

(10) Patent No.: US 12,128,030 B2
(45) Date of Patent: Oct. 29, 2024

(54) PHARMACEUTICAL COMPOSITION COMPRISING ANTIPLATELET AGENT AND GASTRIC ACID SECRETION INHIBITOR

(71) Applicant: HK INNO.N CORPORATION, Seoul (KR)

(72) Inventors: Tae Keun Cho, Incheon (KR); Young Dae Cho, Gyeonggi-do (KR); Eunji Kwon, Seoul (KR); Myung Jin Shin, Seoul (KR)

(73) Assignee: HK INNO.N CORPORATION, Chungcheongbuk-do (KR)

( * ) Notice: Subject to any disclaimer, the term of this patent is extended or adjusted under 35 U.S.C. 154(b) by 861 days.

(21) Appl. No.: 17/271,279

(22) PCT Filed: Aug. 27, 2019

(86) PCT No.: PCT/KR2019/010891
§ 371 (c)(1),
(2) Date: Feb. 25, 2021

(87) PCT Pub. No.: WO2020/045940
PCT Pub. Date: Mar. 5, 2020

(65) Prior Publication Data
US 2021/0251967 A1    Aug. 19, 2021

(30) Foreign Application Priority Data

Aug. 28, 2018   (KR) .......................... 10-2018-0101047

(51) Int. Cl.
*A61K 31/4184*    (2006.01)
*A61K 9/20*    (2006.01)
(Continued)

(52) U.S. Cl.
CPC ........ *A61K 31/4184* (2013.01); *A61K 9/2077* (2013.01); *A61K 9/209* (2013.01); *A61K 9/4866* (2013.01); *A61K 31/4365* (2013.01)

(58) Field of Classification Search
CPC .. A61K 31/4184; A61K 9/2077; A61K 9/209; A61K 9/4866
(Continued)

(56) References Cited

U.S. PATENT DOCUMENTS

| 9,504,678 B2 * | 11/2016 | Goldsmith et al. ...... A61K 9/28 |
| 2004/0067995 A1 | 4/2004 | Wong et al. |

(Continued)

FOREIGN PATENT DOCUMENTS

| JP | 2009-520017 | 5/2009 |
| KR | 10-2008-0112361 | 12/2008 |

(Continued)

OTHER PUBLICATIONS

Takahashi N, Take Y. Tegoprazan, a novel potassium-competitive acid blocker to control gastric acid secretion and motility. Journal of Pharmacology and Experimental Therapeutics. Feb. 1, 2018;364(2):275-86. (Year: 2018).*

(Continued)

*Primary Examiner* — Jeffrey S Lundgren
*Assistant Examiner* — Heather Dahlin
(74) *Attorney, Agent, or Firm* — Giordano Law LLC; David A. Giordano

(57) ABSTRACT

The present invention provides a pharmaceutical composition comprising clopidogrel or pharmaceutically acceptable salts thereof; and tegoprazan or pharmaceutically acceptable salts thereof as an active ingredient. The pharmaceutical composition of the present invention has an advantage of (Continued)

maintaining a medicinal effect of clopidogrel while preventing or treating a side effect of clopidogrel, i.e., gastrointestinal disorders.

19 Claims, 6 Drawing Sheets

(51) Int. Cl.
    *A61K 9/24*         (2006.01)
    *A61K 9/48*         (2006.01)
    *A61K 31/4365*     (2006.01)

(58) Field of Classification Search
    USPC .......................................................... 514/394
    See application file for complete search history.

(56) References Cited

U.S. PATENT DOCUMENTS

| | | |
|---|---|---|
| 2005/0043382 A1 | 2/2005 | Wong |
| 2006/0177504 A1 | 8/2006 | Sundharadas |
| 2007/0142448 A1 | 6/2007 | Hanazawa |
| 2007/0243243 A1 | 10/2007 | Goldsmith et al. |
| 2014/0271816 A1 | 9/2014 | Guilford |
| 2015/0079169 A1 | 3/2015 | Plachetka |

FOREIGN PATENT DOCUMENTS

| | | |
|---|---|---|
| KR | 10-1088247 | 11/2011 |
| KR | 10-2015-0105419 | 9/2015 |
| WO | WO2007115305 | 10/2001 |
| WO | 2007/072146 | 6/2007 |
| WO | 2010009745 | 1/2010 |
| WO | WO2018056697 | 3/2018 |
| WO | WO2018056720 | 3/2018 |

OTHER PUBLICATIONS

Lee CH, Franchi F, Angiolillo DJ. Clopidogrel drug interactions: a review of the evidence and clinical implications. Expert Opinion on Drug Metabolism & Toxicology. Nov. 1, 2020;16(11):1079-96. (Year: 2020).*

Medicines and Healthcare Products Regulatory Agency, Clopidogrel and Proton Pump Inhibitors: Interaction—updated advice, Dec. 11, 2014, https://www.gov.uk/drugsafety-update/clopidogrel-and-proton-pump-inhibitors-interaction-updated-advice.

S. Kheloussi, "Appropriate Use and Safety Concerns of Proton Pump Inhibitors". U.S Pharmacist, 2017, 42(6): 38-42.

Furtado, R.H.d., et al., Drug Interaction Between Clopidogrel and Ranitidine or Omeprazole in Stable Coronary Artery Disease: A Double Blind, Double Dummy, Randomized Study. Am J Cardiovasc Drugs 16, 275-284 (2016).

European Patent Office, Extended European Search Report for EP App. No. 19853580.9, Apr. 12, 2022.

[CJ_APA_107], "An Open-label, Randomized Study to Evaluate Pharmacokinetic Interaction, Pharmacodynamics and Safety After Multiple Oral Dosing of CJ-12420 and Amoxicillin/Clarithromycin in Healthy Subjects", May 2017.

[CJ_APA_110], "A Randomized, Open-label, Three-period, Multiple Dosing Crossover Clinical Trial to Evaluate the Influence of Tegoprazan on the Pharmacodynamics of Clopidogrel According to CYP2C19 Genotypes in Healthy Male Volunteers", Oct. 2019.

[CJ_APA_113], "A Randomized, Open-label, Multiple-dose, Crossover Clinical Trial to Explore the Drug Interaction of Tegoprazan or RAPA113 and Clopidogrel After Oral Administration in Healthy Male Volunteers", May 2020.

[CJ_APA_306], "A Phase 3, Randomized, Double-blind, Active-controlled, Multicenter Study to Evaluate the Efficacy and Safety of a Triple Therapy With CJ-12420, Amoxicillin and Clarithromycin in H. Pylori Positive Patients", Clinicaltrial.gov, Nov. 2017.

Ghim et al., "Pharmacokinetics and Pharmacodynamics of Tegoprazan Coadministered With Amoxicillin and Clarithromycin in Healthy Subjects", The Journal of Clinical Pharmacology, 2020, 0(0), pp. 1-10.

[CJ_APA_303], "A Double Blind, Randomized, Active-controlled, Phase 3 Study to Evaluate the Safety and Efficacy of CJ-12420 in Patients With Gastric Ulcer", Apr. 2018.

Notice of Reason for Refusal issued Feb. 15, 2022 in corresponding Japanese Patent Application No. 2021-510330, with English-language translation.

International Search Report issued Dec. 6, 2019 in corresponding International Patent Application No. PCT/KR2019/010891.

Hulot et al., "Cytochrome P450 2C19 loss-of-function polymorphism is a major determinant of clopidogrel responsiveness in healthy subjects", The American Society of Hematology, Blood, vol. 108, No. 7: pp. 2244-2247 (2006).

Jo, "Drug Interaction between Proton Pump Inhibitors and Clopidogrel: Safe Perspective", the Korean Journal of Internal Medicine: vol. 81, First Issue, 2011, with English abstract.

Oshima and Miwa, "Potent potassium-competitive acid blockers: A new era for the treatment of acid related diseases", Journal of Neurogastroenterology and Motility (2018), vol. 24, No. 3, p. 334-344, DOI:10.5056/jnm18029, Published Jul. 30, 2018.

Inatomi et al., "Potassium-competitive acid blockers: Advanced therapeutic option for acid-related diseases," Pharmacology & Therapeutics 168 (2016) 12-22.

Daewoong Pharmaceutical, "P-CAB (Potassium-competitive acid blocker): Tegoprazan, Bonoprazan, Daewoong Pharmaceutical DWP14012," Apr. 14, 2018, accessed at https://aboutmedicine.tistory.com/30.

* cited by examiner

[Fig. 1]
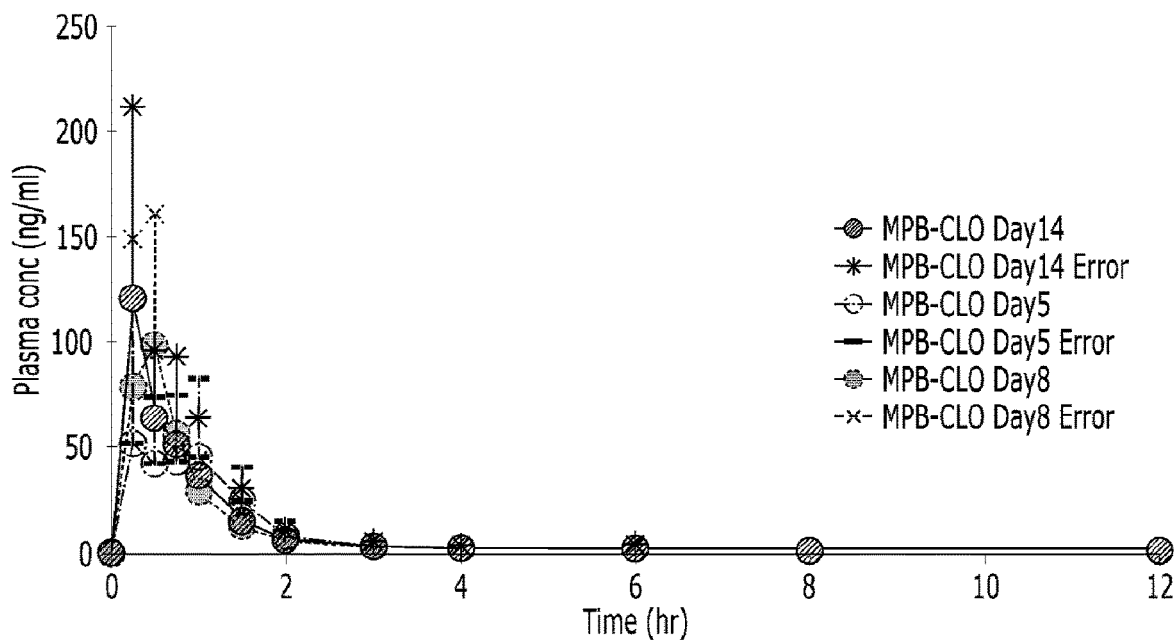
[Fig. 2]
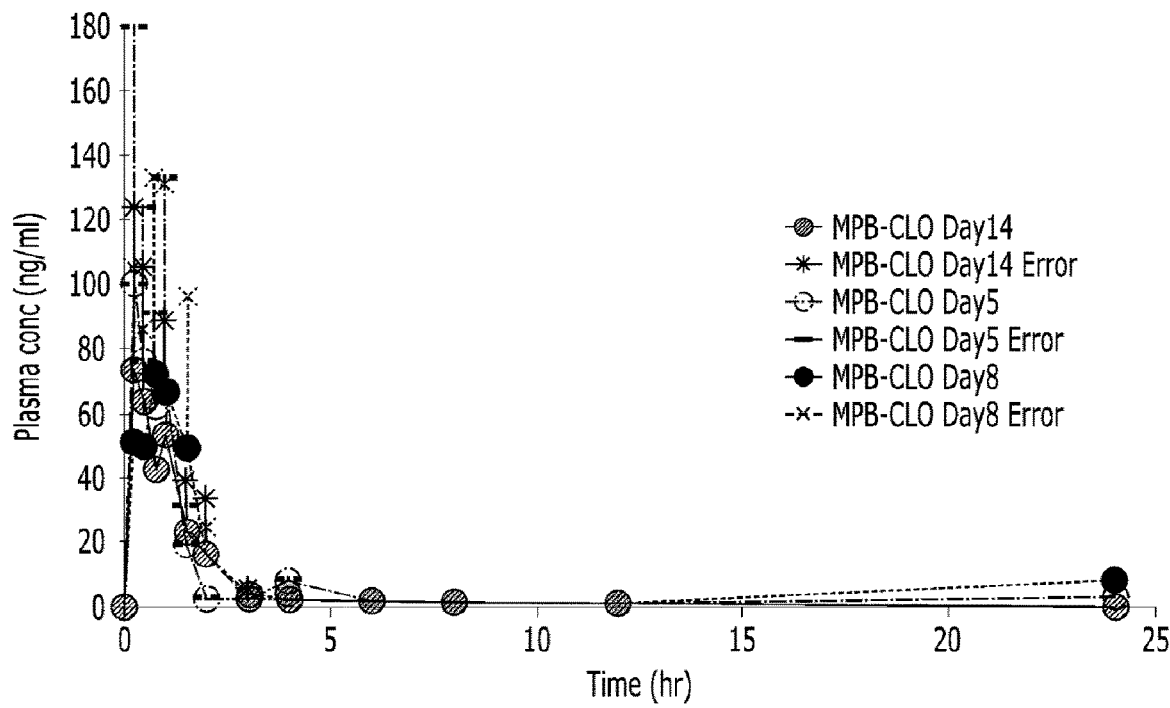

[Fig. 3]
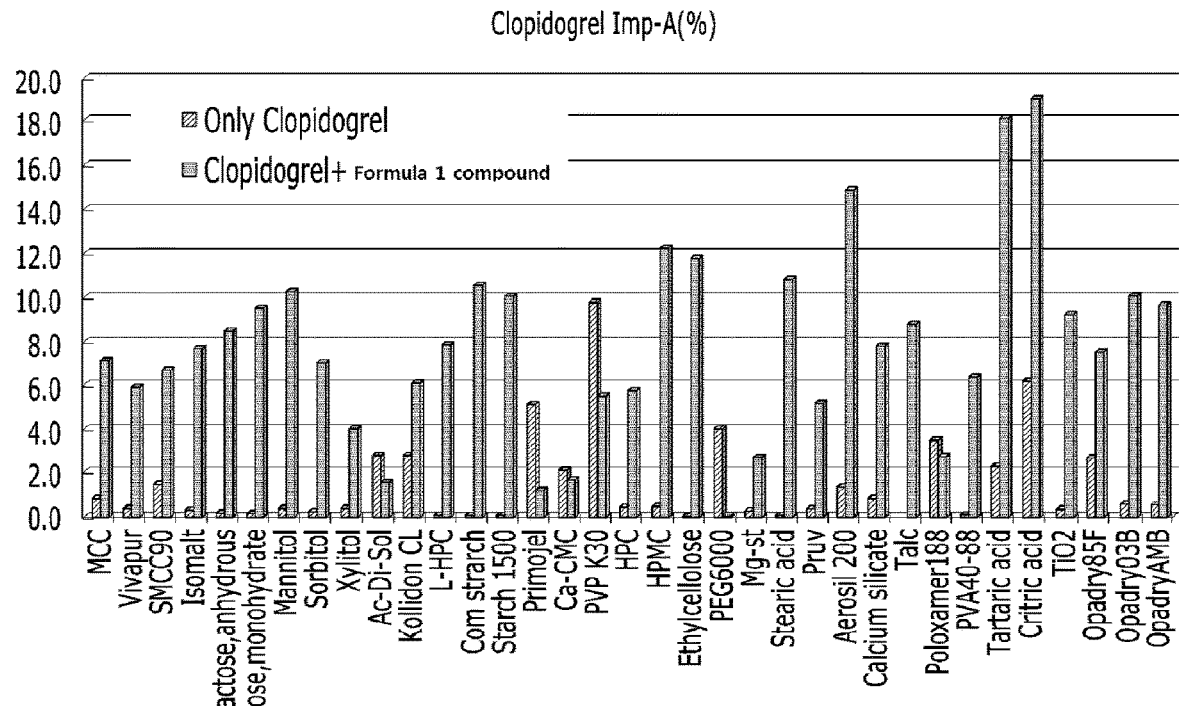
[Fig. 4]
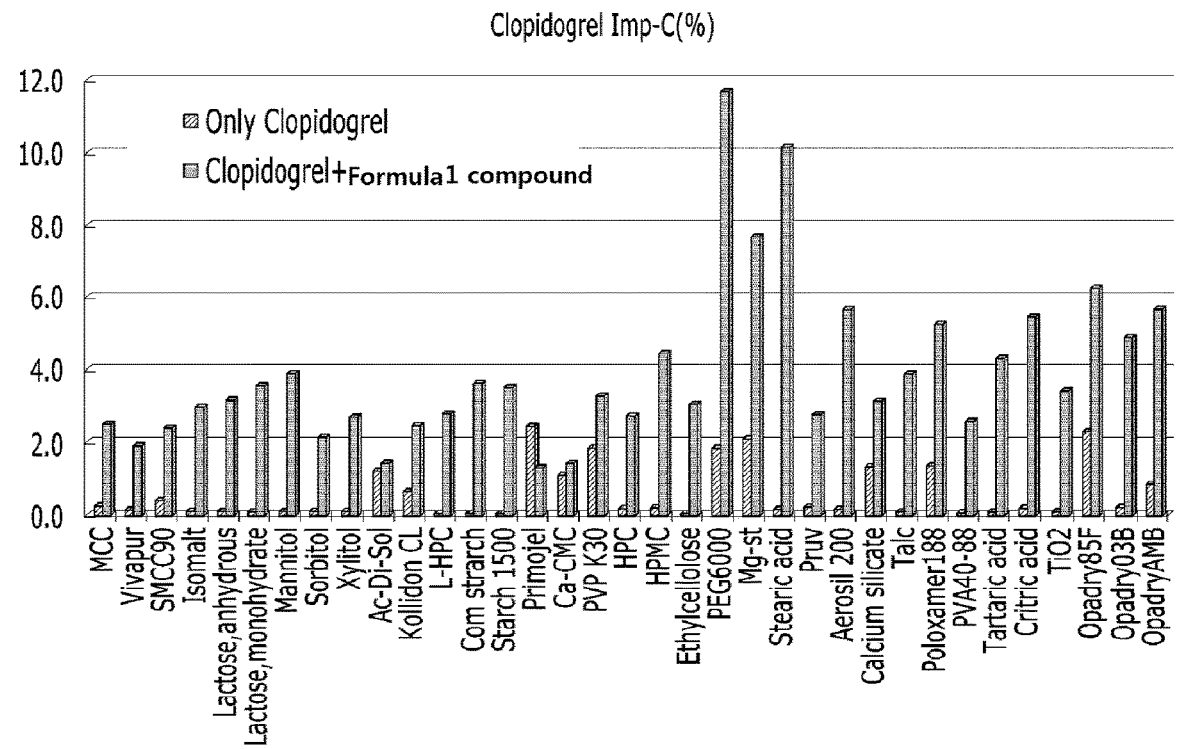

[Fig. 5]
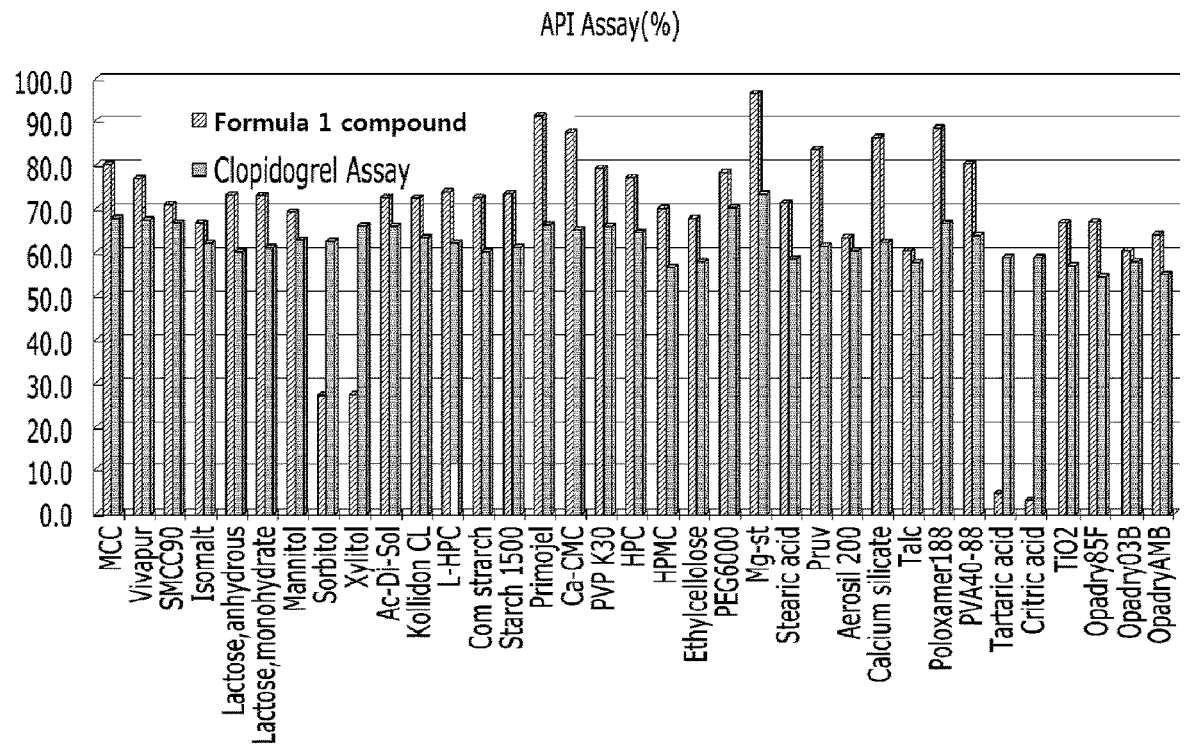
[Fig. 6]
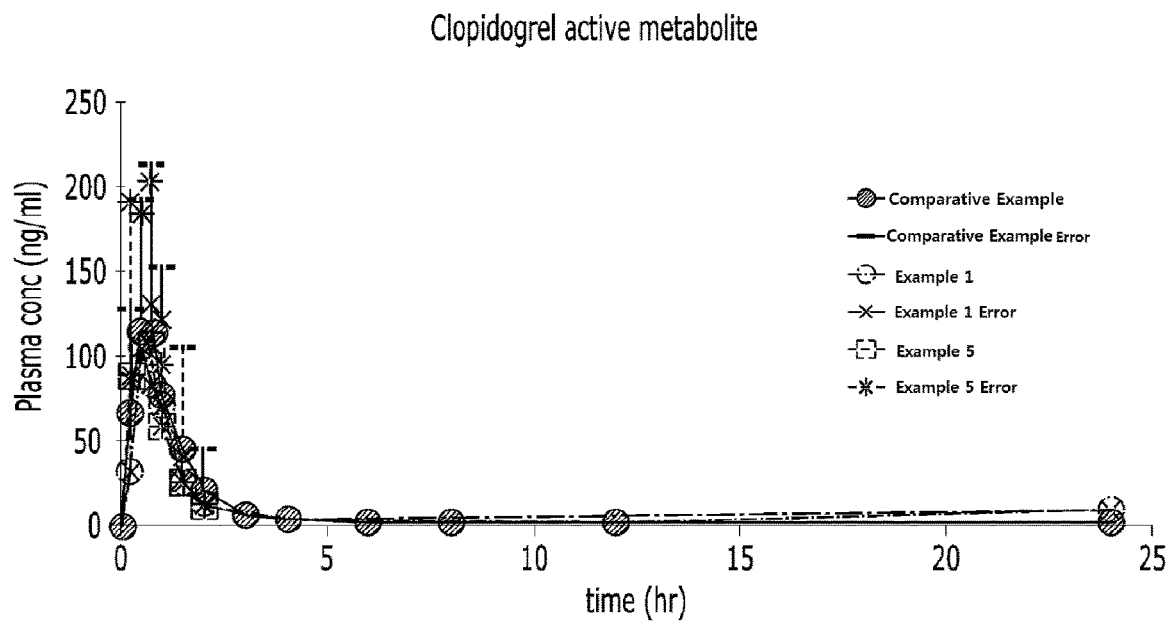

[Fig. 7]
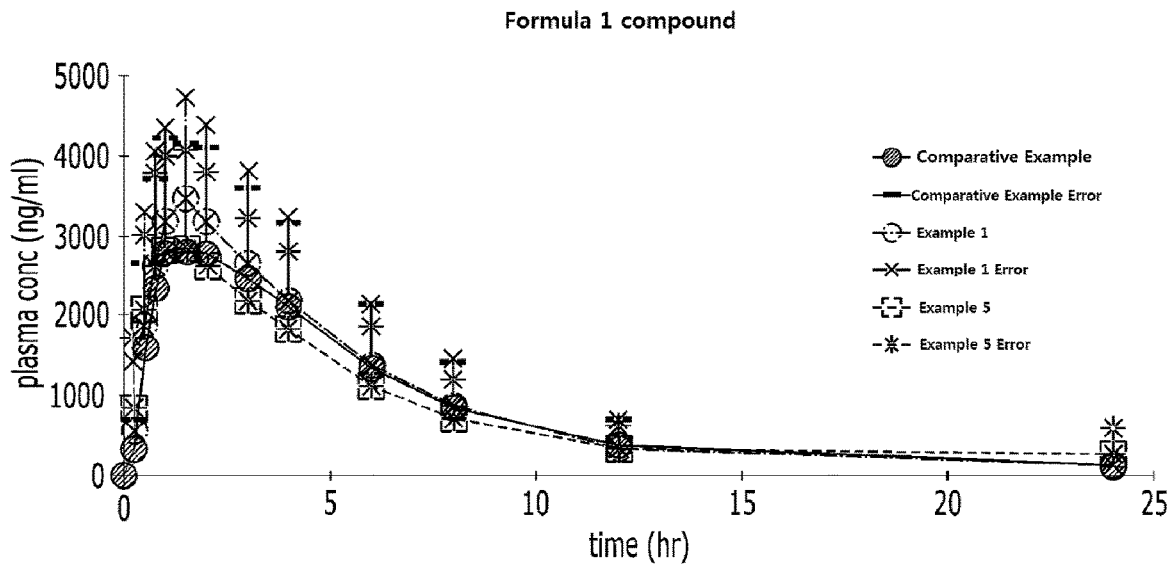
[Fig. 8]
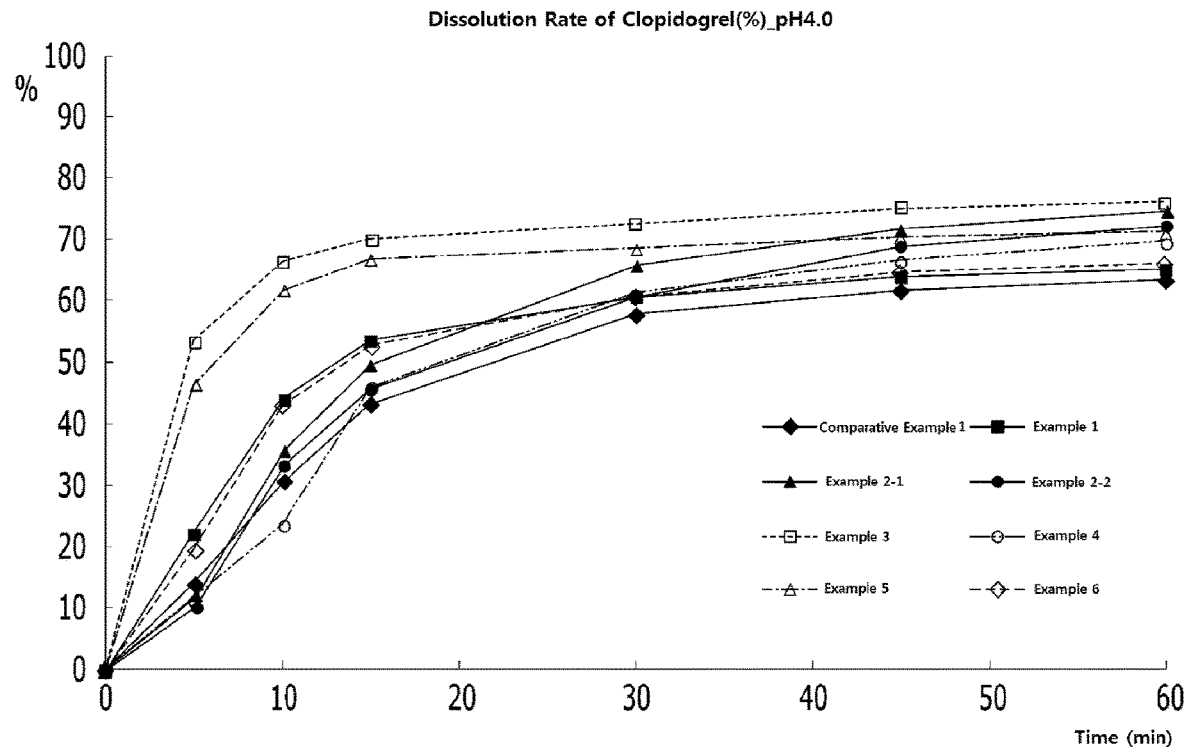

[Fig. 9]
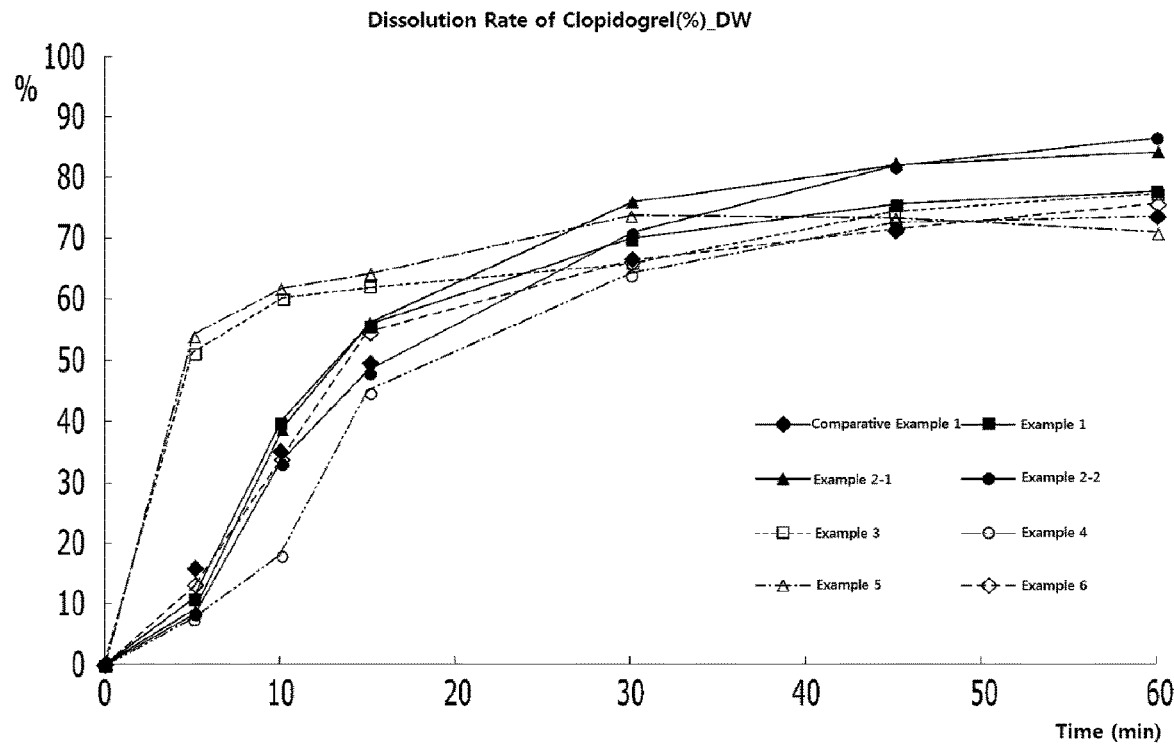
[Fig. 10]
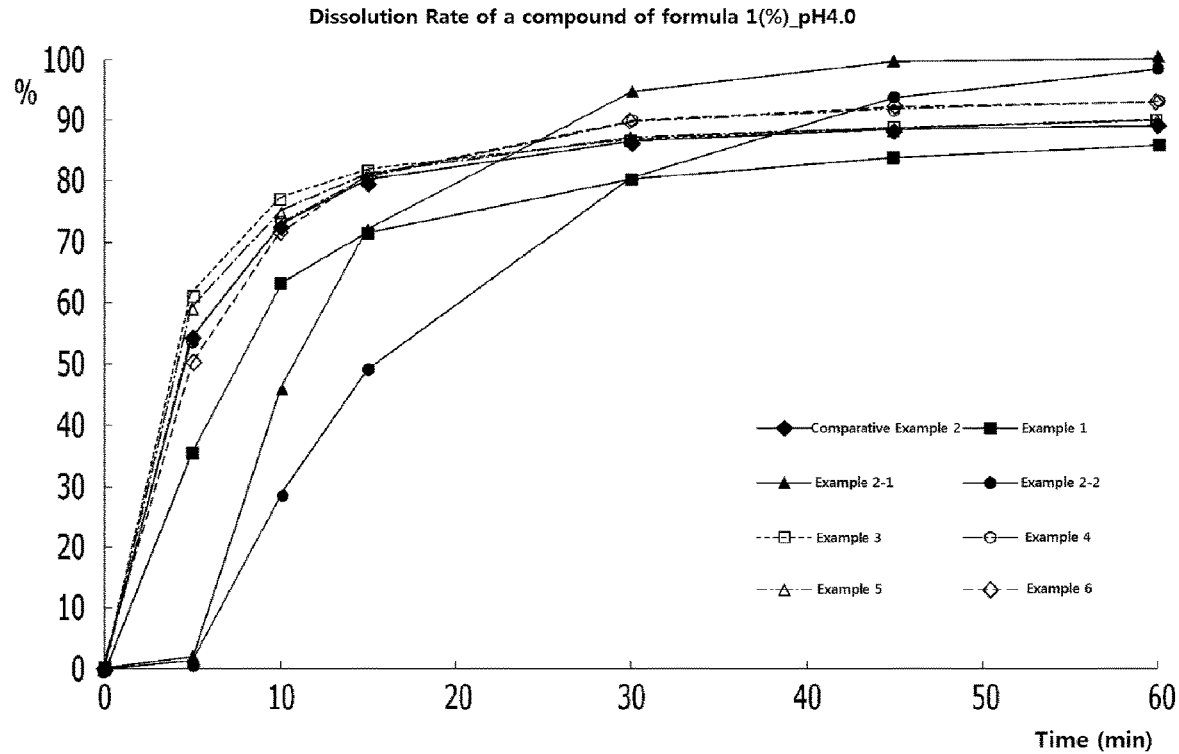

[Fig. 11]
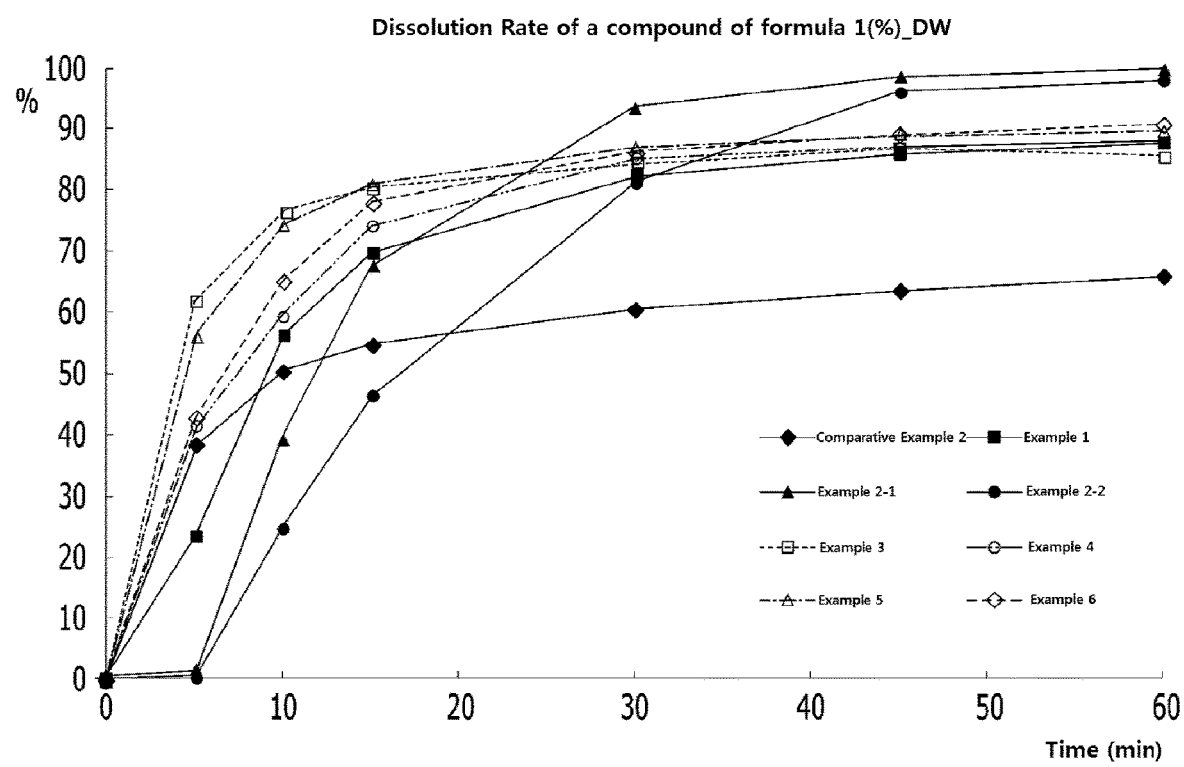

PHARMACEUTICAL COMPOSITION COMPRISING ANTIPLATELET AGENT AND GASTRIC ACID SECRETION INHIBITOR

TECHNICAL FIELD

The present invention relates to a pharmaceutical composition comprising clopidogrel and a compound of Formula 1, and more particularly, to a pharmaceutical composition, which is stable enough to maintain a medicinal effect of clopidogrel while preventing or reducing clopidogrel-related gastrointestinal disorders at the same time, in such a way that clopidogrel is used in combination with the compound of Formula 1.

[Formula 1]

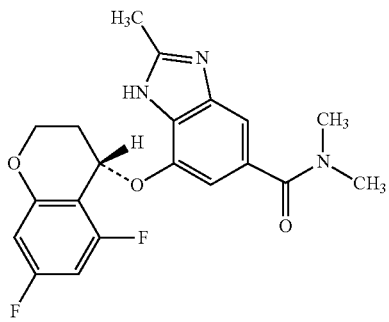

BACKGROUND ART

Clopidogrel is a platelet aggregation inhibitor, which is effective in treating peripheral or coronary arterial diseases such as stroke, thrombosis, embolism or myocardial infarction, wherein a chemical name thereof is methyl (+)-(S)-α-(2-chlorophenyl)-6,7-dihydrothieno[3,2-c]pyridine-5(4H)-acetate.

Clopidogrel specifically inhibits adenosinediphosphate (hereinafter "ADP")-induced platelet aggregation by means of direct inhibition of ADP binding to an ADP receptor, which is known to play an important role in thrombogenesis, and then by means of direct inhibition of ADP-mediated activation of a subsequent glycoprotein GPIIb/IIIa complex. Also, clopidogrel inhibits platelet aggregation caused by agonists except the ADP by blocking the amplification of platelet activation by means of the ADP released. Upon acting on platelets, clopidogrel shows an effect of inhibiting such aggregation until about seven days, when lifetime of such platelets is ended.

Such effect of clopidogrel is an action performed by an active metabolite of clopidogrel. In other words, an enzyme, which metabolizes clopidogrel in the liver, serves as an important factor in the effectiveness of clopidogrel. In early days, it was expected that clopidogrel would be metabolized by CYP1A only, but it has been further found in the latest study that CYP2C19 also serves as an enzyme involved in converting clopidogrel into an active metabolite.

Meanwhile, clopidogrel has a problem of side effects, in that it causes gastrointestinal disorders such as ulcers and gastrointestinal bleeding. Patients who need an antiplatelet drug therapy for a long period of time often suspend such therapy or become ineligible to receive such therapy due to gastrointestinal disorders. In result, such patients may not expect a beneficial treatment effect.

To overcome such side effects as gastrointestinal disorders, there are rare cases in which clopidogrel and proton pump inhibitors (hereinafter "PPI") were prescribed off-label in combination. However, it has been reported in a series of study results that a drug concentration of the active metabolite of clopidogrel becomes low enough to reduce the medicinal effect thereof by half, if clopidogrel is administered in combination with PPI-based drugs (ex. omeprazole, esomeprazole, pantoprazole, lansoprazole, etc.) of inhibiting an activity of CYP2C19. That's because clopidogrel is characterized by having a mechanism, in which clopidogrel is converted into an active metabolite via CYP2C19 to exhibit a medicinal effect.

Accordingly, the U.S. FDA recommended in 2011 that clopidogrel should not be used together with omeprazole. This measure was taken by reflecting a clinical result, in which its concomitant intake with some PPIs would interfere with an action of clopidogrel to increase a risk of cardiac events such as acute myocardial infarction, etc.

Against these backdrops, as a result of making efforts to find a way to overcome gastrointestinal disorders while securing an original medicinal effect of clopidogrel, the present inventors have identified that a use of clopidogrel in combination with a compound of Formula 1 may surprisingly recover an inhibited medicinal effect of clopidogrel, i.e., solving a problem of existing gastric acid secretion inhibitors, while preventing and treating gastrointestinal disorders resulting from clopidogrel, thereby completing the present invention.

PRIOR ART REFERENCE

Prior Art Reference 1: Korean Patent Published No. 10-2008-0112361 "Oral dosage forms including an antiplatelet agent and an acid inhibitor"
Prior Art Reference 2: Korean Patent Published No. 10-2015-0105419 "Oral dosage forms including an antiplatelet agent and an acid inhibitor"
Prior Art Reference 3: Korean Patent Registered No. 10-1088247 "Chromane substituted benzimidazoles and use thereof as acid pump inhibitors"
Prior Art Reference 4: U.S. Patent Published No. 2015/0079169 "Controlled dosing of clopidogrel with gastric acid inhibition therapies"

NON-PATENT DOCUMENT

Non-Patent Document 1: "Cytochrome P450 2C19 loss-of-function polymorphism is a major determinant of clopidogrel responsiveness in healthy subjects." Jean-Sebastein et al., The American Society of Hematology, Blood, 1 Oct. 2006. Vol 108, Number 7.
Non-Patent Document 2: Effect of proton pump inhibitors on drug interactions including antiplatelet agents: safe perspective by the Korean Journal of Internal Medicine: Vol. 81, First Issue, 2011.

DISCLOSURE OF INVENTION

Technical Problem

The present invention provides a pharmaceutical composition comprising clopidogrel or pharmaceutically acceptable salts thereof; and a compound of Formula 1 or pharmaceutically acceptable salts thereof as an active ingredient.

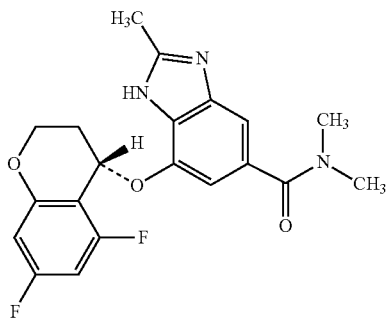

[Formula 1]

The present invention provides a method for preventing or treating thrombogenesis-related diseases, comprising a step of administering a pharmaceutical composition comprising clopidogrel or pharmaceutically acceptable salts thereof; and a compound of Formula 1 or pharmaceutically acceptable salts thereof as an active ingredient into subjects in need.

The present invention provides a use of clopidogrel or pharmaceutically acceptable salts thereof; and a compound of Formula 1 or pharmaceutically acceptable salts thereof for preventing or treating thrombogenesis-related diseases.

The present invention provides a use of clopidogrel or pharmaceutically acceptable salts thereof; and a compound of Formula 1 or pharmaceutically acceptable salts thereof in preparation of a medicament for preventing or treating thrombogenesis-related diseases.

Solution to Problem

This is described in detail as follows. Meanwhile, each description and embodiment disclosed in the present invention may be applied to other descriptions and embodiments thereof, respectively. In other words, all the combinations of various elements disclosed in the present invention fall within the scope of the present invention. Also, it may not be seen that the scope of the present invention is limited to the specific descriptions described below.

According to one aspect of the present invention to achieve the objectives above, there is provided a pharmaceutical composition comprising clopidogrel or pharmaceutically acceptable salts thereof; and a compound of Formula 1 or pharmaceutically acceptable salts thereof as an active ingredient.

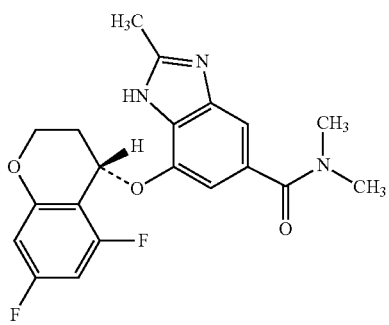

[Formula 1]

The pharmaceutical composition may be one, which comprises clopidogrel or pharmaceutically acceptable salts thereof; and the compound of Formula 1 or pharmaceutically acceptable salts thereof respectively as a separate preparation or contains all thereof in a form of complex preparation. In other words, the pharmaceutical composition may be a combination of separate preparations, or a complex preparation. In case of using clopidogrel or pharmaceutically acceptable salts thereof, and the compound of Formula 1 or pharmaceutically acceptable salts thereof in combination, a medicinal effect of clopidogrel or pharmaceutically acceptable salts thereof may be maintained, while gastrointestinal disorders resulting therefrom may be prevented or treated. Thus, the pharmaceutical composition has an excellent effect on all the diseases, which are known to be prevented or treated by means of conventional clopidogrel. The pharmaceutical composition may be very valuably used, for example, as a composition for antiplatelet therapy. Also, the pharmaceutical composition comprising the compound of Formula 1 or pharmaceutically acceptable salts thereof may be very valuably used for the purpose of preventing or treating gastrointestinal disorders associated with antiplatelet therapy, for example, gastrointestinal disorders caused by administration of clopidogrel.

According to one embodiment of the present invention, the pharmaceutical composition of the present invention may be a preparation for oral administration. The preparation for oral administration may be formulated into capsule preparations (comprising soft and hard capsule preparations); tablets (comprising single-layer tablets, multi-layer tablets, and gastric disintegrating, effervescent and modified release dosage forms); granule preparations; pellet preparations; solvents; suspensions; powders; gels; films for oral administration; or other dosage forms known in the art.

According to another one embodiment of the present invention, a content of the clopidogrel or pharmaceutically acceptable salts thereof may be 10 to 300 mg in the pharmaceutical composition of the present invention.

According to another one embodiment of the present invention, a content of the compound of Formula 1 may be 10 to 200 mg in the pharmaceutical composition of the present invention.

The pharmaceutical composition of the present invention may be described in more detail as follows.

(1) Active Ingredient

As used herein, the term "clopidogrel" refers to methyl (+)-(S)-α-(2-chlorophenyl)-6,7-dihydrothieno[3,2-c]pyridine-5(4H)-acetate, and is particularly represented by Formula X below. Clopidogrel is effectively used as an antiplatelet agent in treating peripheral or coronary arterial diseases such as stroke, thrombosis, embolism or myocardial infarction.

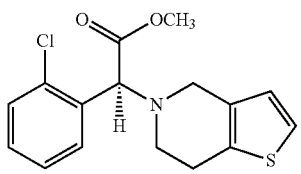

[Formula X]

Clopidogrel directly inhibits adenosinediphosphate (hereinafter "ADP") binding to an ADP receptor, which is known to play an important role in thrombogenesis. Also, clopidogrel specifically inhibits ADP-induced platelet aggregation by directly inhibiting ADP-mediated activation of a subsequent glycoprotein GPIIb/IIa complex. Furthermore, clopidogrel inhibits platelet aggregation caused by agonists except the ADP by blocking the amplification of platelet activation by means of the ADP released.

According to one embodiment of the present invention, the pharmaceutically acceptable salts of the clopidogrel may be selected from the group consisting of clopidogrel hydrogensulfate, resinate, camsylate, besylate, napadisilate monohydrate, hydrochloride and mixtures thereof, but not limited thereto.

In the pharmaceutical composition of the present invention, a content of clopidogrel or pharmaceutically acceptable salts thereof may be 10 to 300 mg, preferably 75 to 300 mg, but not limited thereto.

As used herein, the term "compound of Formula 1" refers to ((S)-4-[(5,7-difluoro-3,4-dihydro-2H-chromene-4-yl)oxy]-N,N,2-trimethyl-1H-benzimidazole-6-carboxamide), is particularly represented by Formula 1 below, and is called tegoprazan.

[Formula 1]

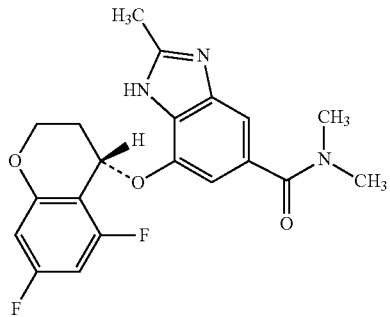

In case of the compound of Formula 1 above, the compound or pharmaceutically acceptable salts thereof as well as optical isomers and racemates showing an efficacy equal thereto are all comprised in the scope herein.

The compound of Formula 1 above is effectively used as a gastric acid secretion inhibitor in treating the diseases mediated by an acid pump antagonistic activity, such as gastrointestinal disease, gastroesophageal disease, gastroesophageal reflux disease (GERD), peptic ulcer, gastric ulcer, duodenal ulcer, NSAID-induced ulcer, gastritis, *Helicobacter pylori* infection, dyspepsia, functional dyspepsia, Zollinger-Ellison syndrome, nonerosive reflux disease (NERD), visceral referred pain, purosis, nausea, esophagitis, dysphagia, salivation, airway lesion or asthma, wherein eligible diseases are not limited to the diseases listed above. The compound of Formula 1 according to the present invention is a potassium-competitive acid blocker (P-CAB).

According to one embodiment of the present invention, the pharmaceutically acceptable salts of the compound of Formula 1 above may comprise acid-addition salts and base-addition salts (comprising dibasic). The acid-addition salts may be, for example, acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate or xinofoate, but not limited thereto. The base-addition salts may be, for example, alkaline metal salts, e.g., lithium salt, sodium salt or potassium salt; alkaline earth metal salts, e.g., calcium salt or magnesium salt; ammonium salts; or organic basic salts, e.g., triethylamine salt, diisopropylamine salt or cyclohexylamine salt, but not limited thereto.

(2) Dosage Form and Administration

The pharmaceutical composition of the present invention may be used, in such a way that such composition is prepared into various forms such as preparations for oral administration such as powders, granule preparations, pellet preparations, tablets, capsule preparations, suspensions, emulsions, syrups, aerosols, etc.; preparations for injection of sterile injectable solution; etc., according to a conventional method suitable for purposes of use.

According to one embodiment of the present invention, the pharmaceutical composition of the present invention is a preparation for oral administration. Also, according to a preferred embodiment of the present invention, the preparation for oral administration is selected from the group consisting of granule preparations, pellet preparations, tablets or capsule preparations.

According to one preferred embodiment of the present invention, the capsule preparations may be one, which is filled with granules or pellets comprising clopidogrel or pharmaceutically acceptable salts thereof. Also, according to one preferred embodiment of the present invention, the capsule preparations may be one, which is filled with granules or pellets comprising a compound of Formula 1 or pharmaceutically acceptable salts thereof. According to another one preferred embodiment of the present invention, the capsule preparations may be one, which is filled with multi-layer coated pellets having one of clopidogrel or pharmaceutically acceptable salts thereof; or the compound of Formula 1 or pharmaceutically acceptable salts thereof in an inner layer thereof.

According to one specific embodiment of the present invention, the capsule preparations are filled with pellets comprising clopidogrel or pharmaceutically acceptable salts thereof; and granules comprising the compound of Formula 1 or pharmaceutically acceptable salts thereof.

According to another specific embodiment of the present invention, the capsule preparations are filled with pellets comprising clopidogrel or pharmaceutically acceptable salts thereof; and the compound of Formula 1 or pharmaceutically acceptable salts thereof. The pellets may comprising all of clopidogrel or pharmaceutically acceptable salts thereof; and the compound of Formula 1 or pharmaceutically acceptable salts thereof in one particle, and may also contain only one of clopidogrel or pharmaceutically acceptable salts thereof; or the compound of Formula 1 or pharmaceutically acceptable salts thereof in one particle, respectively.

According to one specific embodiment of the present invention, the tablets may be a single-layer tablet or a multi-layer tablet. The multi-layer tablet may be, for example, a two-layer tablet or a three-layer tablet, and a layer comprising no active ingredient may be present therein.

According to one embodiment of the present invention, clopidogrel or pharmaceutically acceptable salts thereof and the compound of Formula 1 or pharmaceutically acceptable salts thereof may be prepared into a form without being brought into direct physical contact with each other. Such blocking of physical contact may make it more advantageous to secure stability, for example, in such a way that the production of related substances is minimized by controlling physicochemical reactions or interactions between drugs.

According to one embodiment of the present invention, a combination comprising clopidogrel or pharmaceutically acceptable salts thereof; and the compound of Formula 1 or pharmaceutically acceptable salts thereof may be formed in a kit type. The kit comprises a separate preparation comprising an active ingredient respectively, and may optionally comprise other elements, for example, additional reagents, user's manuals or the like.

The pharmaceutical composition of the present invention may further comprise other antiplatelet agents as an active ingredient, in addition to clopidogrel or pharmaceutically acceptable salts thereof; and the compound of Formula 1 or pharmaceutically acceptable salts thereof. Also, the pharmaceutical composition of the present invention may be administered sequentially or simultaneously with a conventional therapeutic agent, and may be administered in a single or multiple manner.

In the present invention, "administration" means offering an active ingredient to subjects in any appropriate method, and the pharmaceutical composition of the present invention may be administered via all the general routes, as long as such composition may reach a target tissue. Also, the composition of the present invention may be administered with any devices capable of delivering an active ingredient to a target organ.

In the present invention, "subjects" comprise mammals such as humans, guinea pigs, monkeys, cows, horses, sheep, pigs, chickens, turkeys, quails, cats, dogs, mice, rats or rabbits, but not limited thereto, and may be preferably humans.

(3) Pharmaceutically Acceptable Additives

The pharmaceutical composition of the present invention may further comprise pharmaceutically acceptable additives within the range that does not undermine the effect of an active ingredient according to the present invention. As the additives, any pharmaceutically acceptable ones, which are conventionally used in each dosage form, may be also used, for example, fillers, disintegrants, binders, plasticizers, glidants, coating agents (for dampproof or enteric properties), pH adjusting agents, diluents, lubricants, preservatives, buffers, sweetening agents, humectants, suspending agents, coloring agents, flavoring agents, excipients, etc.

According to one specific embodiment of the present invention, granules or pellets comprising clopidogrel or pharmaceutically acceptable salts thereof comprise pharmaceutically acceptable fillers, disintegrants, binders, plasticizers, glidants, coating agents and pH adjusting agents.

According to one specific embodiment of the present invention, granules or pellets comprising the compound of Formula 1 or pharmaceutically acceptable salts thereof comprise pharmaceutically acceptable binders, disintegrants and glidants.

The granules or pellets may be administered in a dosage form of granule preparation or pellet preparation respectively, and may be also administered in such a way that the granules or pellets are filled into capsules or the granules or pellets are compressed and formulated into tablets.

In the present invention, as the fillers, the followings may be used, but not limited thereto: microcrystalline cellulose, methyl cellulose, sodium carboxymethyl cellulose, hydroxypropyl methylcellulose, propylene glycol, lactose, white sugar, glucose, fructose, dextrin, mannitol, sodium alginate, maize starch, potato starch, pregelatinized starch, hydroxypropyl starch, precipitated calcium carbonate, synthetic aluminum silicate, calcium hydrogen phosphate, calcium sulfate, sodium chloride, sodium hydrogen carbonate, purified lanolin, kaolin, urea, colloidal silica gel, casein, primojel, mixtures thereof or the like.

According to a preferred embodiment of the present invention, in granules or pellets comprising clopidogrel or pharmaceutically acceptable salts thereof, the fillers may be selected from the group consisting of microcrystalline cellulose, methyl cellulose, sodium carboxymethyl cellulose, lactose, dextrin, mannitol, white sugar, maize starch, pregelatinized starch, precipitated calcium carbonate and calcium hydrogen phosphate or mixtures thereof.

In the present invention, as the disintegrants, the followings may be used, but not limited thereto: guar gum, xanthan gum, sodium starch glycolate, low-substituted hydroxypropyl cellulose, sodium croscarmellose, microcrystalline cellulose, cross-linked polyvinyl pyrrolidone, maize starch, gelatinized starch, dextran, mannitol, sodium carboxymethyl cellulose and calcium carboxymethyl cellulose, sodium alginate or alginic acid, magnesium aluminum silicate, silicic acid anhydride, bentonite, montmorillonite, veegum, sodium bicarbonate, citric acid, carboxymethyl cellulose, cross-linked polyvinyl pyrrolidone, pre-gelatinized starch, mixtures thereof or the like.

According to a preferred embodiment of the present invention, the disintegrants may be selected from the group consisting of sodium starch glycolate, sodium croscarmellose, hydroxypropyl cellulose, carboxymethyl cellulose, cross-linked polyvinyl pyrrolidone, maize starch or pre-gelatinized starch.

According to a preferred embodiment of the present invention, in granules or pellets comprising clopidogrel or pharmaceutically acceptable salts thereof, the disintegrants may be selected from the group consisting of guar gum, xanthan gum, sodium starch glycolate, low-substituted hydroxypropyl cellulose, sodium croscarmellose, maize starch, gelatinized starch, dextran, sodium carboxymethyl cellulose and calcium carboxymethyl cellulose, magnesium aluminum silicate and silicic acid anhydride and mixtures thereof.

According to a preferred embodiment of the present invention, in granules or pellets comprising the compound of Formula 1 or pharmaceutically acceptable salts thereof, the disintegrants may be selected from the group consisting of sodium starch glycolate, maize starch, bentonite, guar gum, xanthan gum, sodium alginate or alginic acid, low-substituted hydroxypropyl cellulose, microcrystalline cellulose, mannitol, magnesium aluminum silicate, sodium croscarmellose (for example, Ac-Di-Sol®), cross-linked polyvinyl pyrrolidone and mixtures thereof.

In the present invention, as the binders, the followings may be used, but not limited thereto: alginic acid, sodium alginate, carbomer, copovidone, starch, pre-gelatinized starch, polyethylene glycol, polyvinyl pyrrolidone copolymer, polyvinyl derivative, microcrystalline cellulose, methyl cellulose, ethyl cellulose, hydroxyethyl cellulose, hydroxypropyl cellulose, hydroxypropyl methylcellulose, carboxymethyl cellulose and salts thereof, gelatin, gum arabic, sodium caseinate, dextrin, mannitol, lactose, xanthan gum, colloidal silicon dioxide, mixtures thereof or the like.

According to a preferred embodiment of the present invention, in granules or pellets comprising clopidogrel or pharmaceutically acceptable salts thereof, the binders may be selected from the group consisting of alginic acid, carbomer, copovidone, starch, pre-gelatinized starch, polyvinyl derivative, methyl cellulose, ethyl cellulose, hydroxyethyl cellulose, hydroxypropyl cellulose, hydroxypropyl methylcellulose, carboxymethyl cellulose and salts thereof, gelatin, gum arabic and sodium caseinate or mixtures thereof.

According to a preferred embodiment of the present invention, in granules or pellets comprising the compound of Formula 1 or pharmaceutically acceptable salts thereof, the binders may be selected from the group consisting of xanthan gum, sodium alginate, gelatin, gum arabic, dextrin, starch, mannitol, lactose, microcrystalline cellulose, colloidal silicon dioxide, polyethylene glycol, polyvinyl pyrrolidone copolymer, hydroxypropyl cellulose, hydroxypropyl methylcellulose or mixtures thereof.

In the present invention, as the glidants, the followings may be used, but not limited thereto: talc, stearic acid and salts thereof (for example, calcium stearate, magnesium stearate or zinc stearate), sodium stearyl fumarate, silicon dioxide, glyceryl monostearate, polyethylene glycol, sodium benzoate, sodium stearyl fumarate, glyceryl monooleate, glyceryl monostearate, glyceryl behenate, glyceryl palmitostearate, paraffins, mixtures thereof or the like.

According to a preferred embodiment of the present invention, in granules or pellets comprising clopidogrel or pharmaceutically acceptable salts thereof, the glidants may be selected from the group consisting of talc, stearic acid and salts thereof, sodium stearyl fumarate, silicon dioxide, glyceryl monostearate, polyethylene glycol and mixtures thereof.

According to a preferred embodiment of the present invention, in granules or pellets comprising the compound of Formula 1 or pharmaceutically acceptable salts thereof, as the glidants, the followings may be used, but not limited thereto: stearic acid, calcium stearate, magnesium stearate, sodium benzoate, sodium stearyl fumarate, glyceryl monooleate, glyceryl monostearate, glyceryl behenate, glyceryl palmitostearate, zinc stearate, paraffins, etc.

In the present invention, the plasticizers may be selected from the group consisting of glycols, esters, acetyl silicone oil, triethyl citrate, glycerin, glycerin derivative and mixtures thereof.

In the present invention, the coating agents may be selected from the group consisting of methyl cellulose, ethyl cellulose, methyl hydroxyethyl cellulose, sodium carboxymethyl cellulose, hydroxypropyl methylcellulose, hydroxypropyl cellulose, hydroxypropyl methylcellulose phthalate, hydroxyethyl cellulose, cellulose gum, cellulose acetate butyrate, nitrocellulose, salts thereof and mixtures thereof.

In the present invention, the pH adjusting agents comprise organic acid, and the organic acid may be selected from the group consisting of citric acid, hydrochloric acid, lactic acid, phosphoric acid, propionic acid, sulfuric acid, tartaric acid, fumaric acid, malic acid and mixtures thereof.

According to one preferred embodiment of the present invention, the pH adjusting agents may be one or more selected from the group consisting of citric acid, tartaric acid, fumaric acid, lactic acid, phosphoric acid and malic acid.

In the present invention, the diluents may be selected from the group consisting of starch, lactic acid, white sugar, dextrin, dextrose, microcrystalline cellulose, sodium carboxymethyl cellulose, mannitol, sorbitol, xylitol, isomalt, sucrose, calcium hydrogen phosphate, colloidal silicon dioxide or mixtures thereof.

According to a preferred embodiment of the present invention, the diluents may be selected from the group consisting of microcrystalline cellulose, starch, dextrin, lactose, sucrose, mannitol, xylitol, isomalt, sorbitol or mixtures thereof.

According to a preferred embodiment of the present invention, the binders and coating agents may be one or a combination of two or more selected from the group consisting of sodium carboxymethyl cellulose, ethyl cellulose, hydroxypropyl methylcellulose, hydroxypropyl cellulose, hydroxyethyl cellulose, polyvinyl pyrrolidone, xanthan gum, sodium alginate and gelatin.

The scope of the present invention is not limited to use of the additives, and the additives may be contained in a conventional scope of doses by the selection of those skilled in the art.

(4) Therapeutic Method

The present invention also provides a method for preventing or treating thrombogenesis-related diseases from subjects, comprising a step of administering a pharmaceutical composition comprising clopidogrel or pharmaceutically acceptable salts thereof; and a compound of Formula 1 or pharmaceutically acceptable salts thereof as an active ingredient into the subjects in need. The pharmaceutical composition of the present invention is administered in a pharmaceutically effective amount.

In the present invention, "thrombogenesis-related diseases" mean a disease, which may be caused by thrombus-caused blockages in blood vessels, and may refer to stroke, thrombosis, embolism, myocardial infarction or the like, but not limited thereto.

In the present invention, "pharmaceutically effective amount" means an amount enough to treat a disease at a reasonable benefit/risk ratio applicable to medical treatment, and a level of effective amount may be determined according to factors comprising a patient's disease type, severity, activity of a drug, sensitivity to the drug, an administration time, an administration route and excretion rate, a treatment period and a concurrently used drug, as well as other factors well known in a medical field. Considering all the factors above, it is important to carry out an administration by an amount, in which the maximum effect may be achieved by the minimum amount without a side effect, wherein such amount may be easily determined by those skilled in the art.

The pharmaceutical composition of the present invention may be orally administered or administered via various routes comprising intravenous, intraperitoneal, subcutaneous, rectal, local administration, etc., and may be administered into mammals such as humans, rats, mice, livestock, etc.

Particularly, in the composition of the present invention, a daily dosage of clopidogrel or pharmaceutically acceptable salts thereof is 10 to 300 mg, preferably 75 to 300 mg based on adults. Also, in the composition of the present invention, a daily dosage of the compound of Formula 1 or pharmaceutically acceptable salts thereof is 10 to 200 mg based on adults. However, the scope of the present invention is not limited to the dosage.

In the present invention, "prevention" means all the acts, which inhibit or delay the occurrence, spread or recurrence of diseases by means of administration of the composition of the present invention, and "treatment" means all the acts, by which a symptom of diseases gets better or takes a favorable turn by means of administration of the composition of the present invention.

(5) Therapeutic Use

The present invention provides a use of clopidogrel or pharmaceutically acceptable salts thereof; and a compound of Formula 1 or pharmaceutically acceptable salts thereof for preventing or treating thrombogenesis-related diseases. Clopidogrel or pharmaceutically acceptable salts thereof; and the compound of Formula 1 or pharmaceutically acceptable salts thereof for preventing or treating thrombogenesis-related diseases may be combined with acceptable adjuvants, diluents, carriers, etc., and may be prepared into a complex preparation together with other active agents, thus having a synergy action of active components.

(6) Use for Drug Preparation

The present invention provides a use of clopidogrel or pharmaceutically acceptable salts thereof; and a compound of Formula 1 or pharmaceutically acceptable salts thereof in preparation of a medicament for preventing or treating thrombogenesis-related diseases. Clopidogrel or pharmaceutically acceptable salts thereof; and the compound of Formula 1 or pharmaceutically acceptable salts thereof in preparation of a medicament for preventing or treating thrombogenesis-related diseases may be combined with acceptable adjuvants, diluents, carriers, etc., and may be prepared into a complex preparation together with other active agents, thus having a synergy action of active components.

Matters mentioned in the composition, therapeutic method and use of the present invention are applied the same, if not contradictory to each other.

Advantageous Effects of Invention

The present invention exhibits an effect of preventing and treating gastrointestinal disorders resulting from clopidogrel while maintaining a medicinal effect of clopidogrel by using a compound of Formula 1, i.e., a gastric acid secretion inhibitor, in combination with clopidogrel.

BRIEF DESCRIPTION OF DRAWINGS

FIG. 1 is a graph of showing a concentration of clopidogrel in blood upon combined administration of clopidogrel and esomeprazole.

FIG. 2 is a graph of showing a concentration of clopidogrel in blood upon combined administration of clopidogrel and a compound of Formula 1.

FIG. 3 is a result of testing a blending compatibility with clopidogrel-related substance A.

FIG. 4 is a result of testing a blending compatibility with clopidogrel-related substance C.

FIG. 5 is a result of testing a blending compatibility on a content of clopidogrel and a compound of Formula 1.

FIG. 6 is a graph of showing a concentration of clopidogrel in blood.

FIG. 7 is a graph of showing a concentration of a compound of Formula 1 in blood.

FIG. 8 is a graph of showing an elution of clopidogrel at pH 4.0.

FIG. 9 is a graph of showing an elution of clopidogrel in water.

FIG. 10 is a graph of showing an elution of a compound of Formula 1 at pH 4.0.

FIG. 11 is a graph of showing an elution of a compound of Formula 1 in water.

MODE FOR THE INVENTION

Hereinafter, the present invention will be described in more detail through exemplary embodiments. However, these exemplary embodiments are provided only for the purpose of illustrating the present invention, and thus the scope of the present invention is not limited thereto.

Example 1: Capsules Comprising Clopidogrel Pellets and Granules of Compound of Formula 1 all Together A. Preparation for Clopidogrel Pellets Clopidogrel pellets were prepared in accordance with components and contents as shown in a following table 1.

A mixture was prepared in such a way that tartaric acid, hydroxypropyl cellulose, hydroxypropyl methylcellulose, dimethicone and talc were dissolved in ethanol. After that, the pellets were prepared in such a way that the mixture was sprayed onto white sugar spheres with a fluidized bed granulator (GPCG-1, Glatt GmbH, Germany). A mixture, in which clopidogrel hydrogensulfate, hydroxypropyl cellulose, hydroxypropyl methylcellulose, triethyl citrate and talc were dissolved in isopropyl alcohol, was sprayed onto the pellets prepared above with the same equipment, such that the clopidogrel pellets were prepared.

Coating conditions are as follows: Temperature of inflow air at 60±5° C. Temperature of discharging air at 45±5° C. Quantity of air flow at 40±20%, Spray pressure of 1.5±0.5 bar, and Spray velocity of 10±5 g

TABLE 1

| Component name | Quantity (mg) |
| --- | --- |
| White sugar spheres | 50.0 |
| Clopidogrel hydrogensulfate | 97.875 |
| Tartaric acid | 50.0 |
| Hydroxypropyl cellulose | 18.5 |
| Hydroxypropyl methylcellulose | 9.6 |
| Dimethicone | 0.6 |
| Triethyl citrate | 1.0 |
| Talc | 5.425 |

B. Preparation for Granules of Compound of Formula 1

Granules of a compound of Formula 1 were prepared in accordance with components and contents as shown in a following table 2.

The compound of Formula 1, mannitol, microcrystalline cellulose and sodium croscarmellose were mixed together, after which a binder solution comprising hydroxypropyl cellulose and purified water was added into a resulting mixture, such that a kneading and drying process was performed. At the end of drying, size regulation was performed, after which colloidal silicon dioxide and magnesium stearate were mixed together, such that the granules of the compound of Formula 1 were completed.

TABLE 2

| Component name | Quantity (mg) |
| --- | --- |
| Compound of Formula 1 | 50.0 |
| Mannitol | 50.0 |
| Microcrystalline cellulose | 80.0 |
| Sodium croscarmellose | 10.0 |
| Hydroxypropyl cellulose | 6.0 |
| Colloidal silicon dioxide | 2.0 |
| Magnesium stearate | 2.0 |

233 mg of the clopidogrel pellets prepared above and 200 mg of the granules of the compound of Formula 1 were put into hard capsules, such that the capsule preparations of the pharmaceutical composition of the present invention were prepared.

Example 2-1: Preparation for Complex Pellets Comprising Clopidogrel and Compound of Formula 1 Together Complex pellets comprising clopidogrel hydrogensulfate and the compound of Formula 1 were prepared in accordance with components and contents as shown in a following table 3.

A mixture was prepared in such a way that tartaric acid, hydroxypropyl cellulose, hydroxypropyl methylcellulose, dimethicone and talc were dissolved in ethanol, after which the resulting mixture was sprayed onto white sugar spheres with a fluidized bed granulator (GPCG-1, Glatt GmbH, Germany), such that the pellets were prepared. A mixture, in which the compound of Formula 1, hydroxypropyl cellulose, hydroxypropyl methylcellulose, triethyl citrate and talc were dissolved in isopropyl alcohol and ethanol, was sprayed onto the pellets prepared above with the same equipment, such that the pellets of the compound of Formula 1 were prepared. Clopidogrel hydrogensulfate, hydroxypropyl cellulose, hydroxypropyl methylcellulose, triethyl citrate and talc were dissolved in isopropyl alcohol, such that a coating solution was prepared. The pellets of the compound of Formula 1 prepared above were coated with the coating solution by using a fluidized bed granulator, such that complex pellets comprising clopidogrel and the compound of Formula 1 together were prepared.

Coating was performed on the same conditions as shown in Example 1.

TABLE 3

| Component name | Quantity (mg) |
| --- | --- |
| White sugar spheres | 50.0 |
| Clopidogrel hydrogensulfate | 97.875 |
| Compound of Formula 1 | 50.0 |
| Tartaric acid | 50.0 |
| Hydroxypropyl cellulose | 22.5 |
| Talc | 7.625 |
| Hydroxypropyl methylcellulose | 14.7 |
| Dimethicone | 0.6 |
| Triethyl citrate | 1.7 |

Example 2-2: Preparation for Complex Pellets Comprising Clopidogrel and Compound of Formula 1 Together Complex pellets comprising clopidogrel hydrogensulfate and the compound of Formula 1 were prepared in accordance with components and contents as shown in a following table 4.

A compound of Formula 1, hydroxypropyl cellulose, hydroxypropyl methylcellulose, triethyl citrate and talc were dissolved in solvent, i.e., isopropyl alcohol and ethanol, such that a coating solution was prepared. The coating solution prepared above by using a fluidized bed granulator (GPCG-1, Glatt GmbH, Germany) was sprayed onto white sugar spheres, such that the pellets of the compound of Formula 1 were prepared. A mixture, in which tartaric acid, hydroxypropyl cellulose, hydroxypropyl methylcellulose, dimethicone and talc were dissolved in ethanol, was sprayed onto the pellets of the compound of Formula 1 prepared to carry out coating. Clopidogrel hydrogensulfate, hydroxypropyl cellulose, hydroxypropyl methylcellulose, triethyl citrate and talc were dissolved in isopropyl alcohol to prepare a coating solution, after which the pellets prepared above were further coated with the coating solution, such that the complex pellets comprising clopidogrel and the compound of Formula 1 together were prepared.

Coating was performed on the same conditions as shown in Example 2-1.

TABLE 4

| Component name | Quantity (mg) |
| --- | --- |
| White sugar spheres | 50.0 |
| Clopidogrel hydrogensulfate | 97.875 |
| Compound of Formula 1 | 50.0 |
| Tartaric acid | 25.0 |
| Hydroxypropyl cellulose | 22.0 |
| Talc | 7.625 |
| Hydroxypropyl methylcellulose | 14.1 |
| Dimethicone | 0.6 |
| Triethyl citrate | 1.8 |

Examples 3-5. Single-Layer and Two-Layer Tablets Comprising Granules of Clopidogrel and Compound of Formula 1

To prepare a dosage form according to the present invention, the granules comprising clopidogrel were prepared as follows.

TABLE 5

| | Example 3 | Example 4 | Example 5 |
| --- | --- | --- | --- |
| | Dosage form | | |
| | Single-layer tablet | Two-layer tablet | Two-layer tablet |
| Component name | Quantity (unit: mg) | | |
| Clopidogrel hydrogensulfate | 97.875 | Same as left | 97.875 |
| Microcrystalline cellulose | 124.125 | | 61.125 |
| Mannitol | — | | 40.0 |
| Sodium croscarmellose | 15.0 | | 19.0 |
| Hydroxypropyl methylcellulose | 15.0 | | 15.0 |
| Colloidal silicon dioxide | 3.0 | | 3.0 |
| Talc | — | | 3.0 |
| Sodium stearyl fumarate | 5.0 | | — |
| B of Example 1 | 200.0 | | 200.0 |

Clopidogrel hydrogensulfate, microcrystalline cellulose, mannitol and sodium croscarmellose were mixed together in accordance with components and contents as shown in the table 5, after which a binder solution having hydroxypropyl methylcellulose dissolved in acetone/water mixed solution, was added into a resulting mixture, such that a coating and drying process for the granules was performed. At the end of drying, size regulation was performed, after which microcrystalline cellulose, sodium croscarmellose, colloidal silicon dioxide and sodium stearyl fumarate were mixed together, such that the granules of clopidogrel were completed.

The clopidogrel granules prepared above and the granules of the compound of Formula 1 made in B of Example 1 were compressed and prepared into tablets as follows.

1) Example 3: Tablet compression after mixing clopidogrel granules and granules of the compound of Formula 1 together 2) Examples 4-5: Tablet compression into two-layer tablets by forming clopidogrel granules (first layer) and granules of the compound of Formula 1 (second layer)

Example 6: Multi-Layer Tablets Comprising Clopidogrel Granules and Granules of Compound of Formula 1 all Together Compositional property of granules comprising clopidogrel was as shown in a table 6, and a preparation method thereof was performed the same as shown in Examples 3-5.

TABLE 6

| Component name | Quantity (unit: mg) |
| --- | --- |
| Clopidogrel hydrogensulfate | 97.875 |
| Microcrystalline cellulose | 112.125 |
| Sodium croscarmellose | 20.0 |
| Hydroxypropyl methylcellulose | 15.0 |
| Colloidal silicon dioxide | 5.0 |
| Sodium stearyl fumarate | 5.0 |
| Intermediate layer of pharmaceutical additives | 50.0-100.0 |
| B of Example 1 | 200.0 |

The clopidogrel granules prepared above, the granules of the compound of Formula 1 prepared in B of Example 1, and the intermediate layer of pharmaceutical additives were compressed and prepared into multi-layer tablets. For the intermediate layer of pharmaceutical additives, all the conventionally used additives may be used as follows: microcrystalline cellulose, lactose, mannitol, starch, low-substituted hydroxypropyl cellulose and the like, which were proven satisfactory as a result of testing a blending compatibility with two drugs.

Experimental Example 1: Evaluation Test on Drug Interactions Through Nonclinical Models To determine the effect of esomeprazole (PPI drug) and a compound of Formula 1 on a medicinal effect of clopidogrel, a test on pharmacokinetic drug interactions was performed in such a way that 20 mg of clopidogrel and 20 mg of esomeprazole or 50 mg of the compound of Formula 1 were administered in combination into beagle dogs once or repeatedly (for seven days).

Particularly, clopidogrel was repeatedly administered into ten beagle dogs for seven days, after which esomeprazole and the compound of Formula 1 were administered in combination into those beagle dogs at steady-state for seven days, such that blood was collected therefrom on 5th, 8th and 14th days, to perform a pharmacokinetic analysis before and after the administration.

The results thereof are shown in FIGS. 1 to 2. FIGS. 1 and 2 are graphs of showing a concentration of clopidogrel active metabolites in blood, which was measured after administering esomeprazole and the compound of Formula 1 in combination, respectively. It was shown that AUC of clopidogrel active metabolites is at a level of 85% upon repeated administration in combination with esomeprazole and that AUC of clopidogrel active metabolites is 120% upon repeated administration in combination with the compound of Formula 1. Thus, it was identified that there is a low risk of drug interactions between clopidogrel and the compound of Formula 1.

Experimental Example 2: Blending Compatibility Test

A test on blending compatibility with additives was performed in a state, in which clopidogrel was alone and mixed with a compound of Formula 1.

A ratio of additives to main component was adjusted, after which a change of contents and related substances was evaluated under accelerated test conditions (40° C./RH 75%) for four weeks, such that the results thereof are shown in FIGS. 3 to 5.

As a result of considering the results shown in FIGS. 3 to 5 above, it might be seen that the stability of a drug deteriorates due to a eutectic phenomenon between two components, if clopidogrel is brought into direct contact with the compound of Formula 1 despite the selection of additives capable of securing the stability of clopidogrel.

Experimental Example 3: Pharmacokinetic Evaluation of Complex Preparation of Clopidogrel and Compound of Formula 1 on Beagle Dogs A pharmacokinetic evaluation was performed on Example 1 (capsules comprising clopidogrel pellets and granules of the compound of Formula 1) and Example 5 (multi-layer tablets comprising clopidogrel granules and granules of the compound of Formula 1), which are different complex preparation types in the present invention. Plavix Tab. (Comparative Example 1) and the compound of Formula 1 50 mg Tab. (Comparative Example 2) were used as Comparative Example.

Particularly, a test on 12 beagle dogs was organized under conditions of single dose, fasting, 3×3 and crossover design, and the results of evaluating the blood concentrations of clopidogrel metabolites and the compound of Formula 1 on Comparative Examples and Examples are shown in FIGS. 6 and 7.

It was shown that AUC of Example 1 is 96% and AUC of Example 5 is 101% based on AUC of Comparative Example 1. Accordingly, it was identified that various dosage forms of the complex pharmaceutical composition comprising clopidogrel and the compound of Formula 1 are implemented while solving a problem of reduced medicinal effect of clopidogrel, and thus it might be seen that the objectives of the present invention are achieved.

Experimental Example 4: Comparative Elution Test

A comparative elution test was performed with the Method II (Paddle Method) of the elution testing method out of the general testing methods in the Korean Pharmacopoeia (KP). An analysis was performed with the HPLC method under the condition that a volume of eluate was 900 mL; a paddle rotation speed was 50 rpm; a temperature was 37±0.5° C. and a detection wavelength was 240, 262 nm. In the comparative elution test, Plavix Tab. (Comparative Example 1) and the compound of Formula 150 mg Tab. (Comparative Example 2) were used as Comparative Group.

After the initiation of elution, a comparative evaluation was made with an accumulated elution rate for 60 minutes, and the elution rate at pH 4.0 is shown in FIGS. 8 and 10, while the elution rate in water is shown in FIGS. 9 and 11.

Experimental Example 5: Stability Test

A stability evaluation for one month on Examples above was performed under accelerated conditions (40° C. and the results thereof are shown in a table 7. All the prepared Examples satisfied the required criteria for stability.

TABLE 7

|  |  |  | Comparative Example 1 | Comparative Example 2 | Example 1 | Example 2-1 | Example 3 | Example 4 | Example 5 |
|---|---|---|---|---|---|---|---|---|---|
| Clopidogrel hydrogensulfate | Related substance A (%) | Initial | N/D | — | 0.01 | N/D | N/D | N/D | 0.03 |
|  |  | 1 month | 0.03 | — | 0.03 | 0.03 | 0.09 | 0.11 | 0.30 |
|  | Related substance C (%) | Initial | 0.29 | — | N/D | N/D | N/D | N/D | 0.02 |
|  |  | 1 month | 0.30 | — | N/D | 0.01 | 0.07 | 0.06 | 0.06 |
| Compound of Formula 1 | Related substance 1 (%) | Initial | — | 0.10 | 0.11 | 0.11 | 0.10 | 0.10 | 0.10 |
|  |  | 1 month | — | 0.09 | 0.15 | 0.15 | 0.15 | 0.15 | 0.11 |
|  | Related substance 2 (%) | Initial | — | 0.01 | 0.03 | 0.03 | 0.02 | 0.01 | 0.05 |
|  |  | 1 month | — | N/D | 0.05 | 0.09 | 0.06 | 0.03 | 0.01 |
|  | Related substance 3 (%) | Initial | — | N/D | N/D | N/D | N/D | N/D | N/D |
|  |  | 1 month | — | N/D | N/D | 0.01 | 0.01 | N/D | N/D |

Experimental Example 6: Stability Test

A stability evaluation for six months on Examples 1 and 6 above was performed under actual storage conditions, and satisfied all the criteria for stability.

From the description above, those skilled in the art, to which the present invention pertains, will understand that the present invention may be practiced in other specific forms without changing the technical spirit or essential features thereof. In this regard, it should be understood that

TABLE 8

|  |  |  |  | Long-term conditions (25° C.) | | Accelerated conditions (40° C.) | |
|---|---|---|---|---|---|---|---|
|  |  |  | Initial | 3 months | 6 months | 3 months | 6 months |
| Example 1 | Clopidogrel hydrogensulfate | Content (%) | 98.4 | 98.0 | 99.9 | 96.7 | 98.9 |
|  |  | Related substance 1 (%) | 0.01 | 0.01 | 0.03 | 0.02 | 0.04 |
|  |  | Related substance 2 (%) | 0.05 | 0.14 | 0.13 | 0.16 | 0.15 |
|  | Compound of Formula 1 | Content (%) | 99.2 | 98.8 | 99.7 | 96.8 | 98.1 |
|  |  | Related substance 1 (%) | 0.11 | 0.12 | 0.20 | 0.11 | 0.20 |
|  |  | Related substance 2 (%) | 0.04 | 0.08 | 0.06 | 0.12 | 0.06 |
|  |  | Related substance 3 (%) | N/D | N/D | N/D | N/D | N/D |
| Example 6 | Clopidogrel hydrogensulfate | Content (%) | 102.5 | 102.3 | 101.9 | 100.9 | 102.9 |
|  |  | Related substance 1 (%) | 0.01 | 0.01 | 0.02 | 0.01 | 0.05 |
|  |  | Related substance 2 (%) | 0.07 | 0.19 | 0.12 | 0.22 | 0.31 |
|  | Compound of Formula 1 | Content (%) | 100.1 | 99.3 | 99.3 | 97.2 | 99.2 |
|  |  | Related substance 1 (%) | 0.11 | 0.12 | 0.12 | 0.11 | 0.12 |
|  |  | Related substance 2 (%) | 0.04 | 0.06 | 0.06 | 0.09 | 0.06 |
|  |  | Related substance 3 (%) | N/D | N/D | N/D | N/D | N/D | the exemplary embodiments described above are illustrative in all aspects and are not contrived to limit the scope of the present invention. It should be understood that the scope of the present invention comprises all the modifications or changed forms derived from the meaning and scope of the patent claims to be described below as well as equivalents thereto, rather than the detailed descriptions above.

INDUSTRIAL APPLICABILITY

The present invention is characterized by exhibiting an effect of preventing and treating gastrointestinal disorders resulting from clopidogrel while maintaining a medicinal effect of clopidogrel, in such a way that clopidogrel is used in combination with a compound of Formula 1, i.e., a gastric acid secretion inhibitor. Thus, it is expected that the present invention may be valuably used in the related pharmaceutical industry.

The invention claimed is:

1. A pharmaceutical composition comprising clopidogrel or a pharmaceutically acceptable salt thereof, and a compound of Formula 1 or a pharmaceutically acceptable salt thereof,

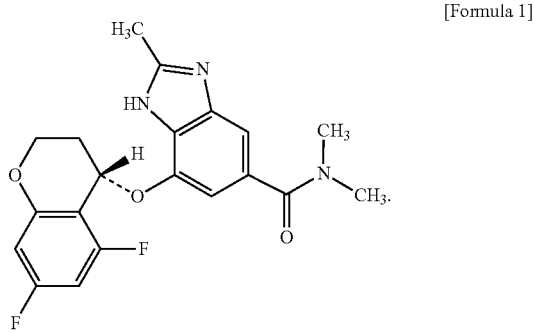 [SMILES: Cc1nc2cc(C(=O)N(C)C)cc(O[C@H]3CCOc4cc(F)cc(F)c43)c2[nH]1]

[Formula 1]

2. The pharmaceutical composition according to claim 1, wherein a content of clopidogrel or pharmaceutically acceptable salt thereof is 10 to 300 mg.

3. The pharmaceutical composition according to claim 1, wherein a content of the compound of Formula 1 or pharmaceutically acceptable salt thereof is 10 to 200 mg.

4. The pharmaceutical composition according to claim 1, wherein the composition is a combination or a complex preparation.

5. The pharmaceutical composition according to claim 1, wherein the composition is a preparation for oral administration.

6. The pharmaceutical composition according to claim 5, wherein the preparation for oral administration is a granule preparation, pellet preparation, tablet or capsule preparation.

7. The pharmaceutical composition according to claim 1, wherein the composition further comprises pharmaceutically acceptable additives.

8. The pharmaceutical composition according to claim 1, wherein the composition further comprises one or more additives selected from the group consisting of diluents, disintegrants, binders, pH adjusting agents, glidants and coating agents.

9. The pharmaceutical composition according to claim 8, wherein the diluent is selected from the group consisting of microcrystalline cellulose, starch, dextrin, lactose, sucrose, mannitol, xylitol, isomalt and sorbitol.

10. The pharmaceutical composition according to claim 8, wherein the disintegrant is selected from the group consisting of sodium starch glycolate, sodium croscarmellose, hydroxypropyl cellulose, carboxymethyl cellulose, cross-linked polyvinyl pyrrolidone, maize starch or pre-gelatinized starch.

11. The pharmaceutical composition according to claim 8, wherein the binders and coating agents are one or a combination of two or more selected from the group consisting of sodium carboxymethyl cellulose, ethyl cellulose, hydroxypropyl methylcellulose, hydroxypropyl cellulose, hydroxyethyl cellulose, polyvinyl pyrrolidone, xanthan gum, sodium alginate and gelatin.

12. The pharmaceutical composition according to claim 8, wherein the pH adjusting agent is organic acid.

13. The pharmaceutical composition according to claim 12, wherein the organic acid is selected from the group consisting of citric acid, tartaric acid, fumaric acid, lactic acid, phosphoric acid and malic acid.

14. The pharmaceutical composition according to claim 6, wherein the capsule preparation comprises granules or pellets comprising clopidogrel or a pharmaceutically acceptable salt thereof.

15. The pharmaceutical composition according to claim 6, wherein the capsule preparation comprises granules or pellets comprising a compound of Formula 1 or a pharmaceutically acceptable salt thereof.

16. The pharmaceutical composition according to claim 6, wherein the capsule preparation comprises at least one multi-layer coated pellet comprising clopidogrel or a pharmaceutically acceptable salt thereof or a compound of Formula 1 or a pharmaceutically acceptable salt thereof in an inner layer of the pellet.

17. The pharmaceutical composition according to claim 4, wherein the complex preparation is configured so that clopidogrel or a pharmaceutically acceptable salt thereof does not contact a compound of Formula 1 or a pharmaceutically acceptable salt thereof.

18. The pharmaceutical composition according to claim 4, wherein the combination is a kit type.

19. A method for preventing or treating a thrombogenesis-related disease in a subject, comprising administering to a subject in need thereof a pharmaceutical composition comprising clopidogrel or a pharmaceutically acceptable salt thereof and a compound of Formula I or a pharmaceutically acceptable salt thereof,

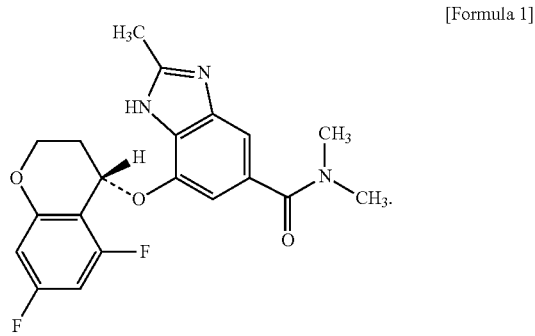 [SMILES: Cc1nc2cc(C(=O)N(C)C)cc(O[C@H]3CCOc4cc(F)cc(F)c43)c2[nH]1]

[Formula 1]

* * * * *